(12) United States Patent
Chu (10) Patent No.: US 8,348,862 B2
(45) Date of Patent: Jan. 8, 2013

(54) MUSCULAR ENERGY STATE ANALYSIS SYSTEM AND METHOD FOR SWING MOTION AND COMPUTER PROGRAM PRODUCT THEREOF

(75) Inventor: Tun-Hsiao Chu, Kaohsiung (TW)

(73) Assignee: Institute for Information Industry, Taipei (TW)

( * ) Notice: Subject to any disclaimer, the term of this patent is extended or adjusted under 35 U.S.C. 154(b) by 339 days.

(21) Appl. No.: 12/634,190

(22) Filed: Dec. 9, 2009

(65) Prior Publication Data
US 2011/0118621 A1    May 19, 2011

(30) Foreign Application Priority Data
Nov. 13, 2009 (TW) ................................ 98138564 A (51) Int. Cl.
| | |
|---|---|
| A61B 5/103 | (2006.01) |
| A61B 5/117 | (2006.01) |
| A61B 5/04 | (2006.01) |
| A61B 5/22 | (2006.01) |
| A61B 1/24 | (2006.01) |
| A63B 57/00 | (2006.01) |
| A63B 69/00 | (2006.01) |
| A63B 69/38 | (2006.01) |
| A63B 53/00 | (2006.01) |
| A63B 21/00 | (2006.01) |
| A63B 21/23 | (2006.01) |
| A63B 23/16 | (2006.01) |
| G01L 3/24 | (2006.01) |
| G01L 5/00 | (2006.01) |

(52) U.S. Cl. ........ 600/587; 600/546; 600/595; 473/219; 473/453; 473/461; 73/65.03; 73/379.01; 73/379.02

(58) Field of Classification Search ................. 600/546, 600/587, 595; 463/2, 3, 47.2; 473/131, 207, 473/219, 282, 453, 457, 461, 463, 524, 564; 73/65.01, 65.03, 65.07, 65.08, 379.01, 379.02
See application file for complete search history.

(56) References Cited

U.S. PATENT DOCUMENTS

| | | | | | |
|---|---|---|---|---|---|
| 5,361,775 | A | * | 11/1994 | Remes et al. ................. | 600/546 |
| 6,148,280 | A | * | 11/2000 | Kramer ......................... | 702/153 |
| 2006/0099556 | A1 | * | 5/2006 | Yeo et al. ...................... | 434/247 |

* cited by examiner

Primary Examiner — Jeffrey G Hoekstra
Assistant Examiner — Devin Henson
(74) Attorney, Agent, or Firm — Muncy, Geissler, Olds & Lowe, PLLC (57) ABSTRACT

A muscular energy state analysis system and method for a swing motion and a computer program product thereof are provided. The system includes: a swing implement, for a user to perform the swing motion, and including an acceleration sensor for sensing acceleration of the swing implement when the swing implement is swung, so as to generate a swing speed data; a plurality of signal detection modules, for detecting electromyographic (EMG) signals generated by a muscles of the user; a database, for storing a muscular energy sample value,; a muscular energy analysis module, for analyzing the EMG signals and the swing speed data so as to obtain a plurality of muscular performance values; and a comparison module, for comparing the swing speed data and the muscular performance values with the at least one muscular energy sample value in the database, so as to generate a comparison result data.

17 Claims, 8 Drawing Sheets

|  | iEMG | | | | muscular performance (%) | | | |
|---|---|---|---|---|---|---|---|---|
|  | A | B | C | D | Force | A | B | C | D | Force |
| User | 0.35 | 0.25 | 0.30 | 0.1 | 1 | 25% | 25% | 30% | 25% | 1 |
| Sample | 0.25 | 0.25 | 0.35 | 0.15 | 1 | 25% | 25% | 35% | 15% | 1 |

MUSCULAR ENERGY STATE ANALYSIS SYSTEM AND METHOD FOR SWING MOTION AND COMPUTER PROGRAM PRODUCT THEREOF

CROSS-REFERENCE TO RELATED APPLICATION

This application claims the benefit of Taiwan Patent Application No. 098138564, filed on Nov. 13, 2009, which is hereby incorporated by reference for all purposes as if fully set forth herein.

BACKGROUND OF THE INVENTION

1. Field of Invention

The present invention relates to a muscular energy state analysis system and method for a swing motion and a computer program product thereof, and more particularly to a muscular energy state analysis system and method for a swing motion by using electromyographic (EMG) signals and swing speed data to analyze a swing motion of a user, and a computer program product thereof.

2. Related Art

In the prior art, EMG signals are commonly used for analyzing the muscular response and force of a user's motion in the filed of medical technology, including training in body rehabilitation for patients, training in using artificial limbs, body balance training for paralyzed patients, and the like. In addition, detection of muscular movements of internal organs such as detection of the response of the cardiac muscle and lung and chest muscles can also employ the EMG signal detection technology, but the EMG signal technology is seldom applied in the field of sports.

In fact, during training, a player needs to pay attention to whether relevant muscles exert forces correctly while preventing muscle injuries caused by overtraining. Swing motions are taken as an example. A swing motion refers to a series of actions that require instantaneous movement of a plurality of muscles, which focuses on muscular powers and coordination of the muscles. Current technologies are mostly only capable of obtaining muscular energy analysis data, but cannot display and analyze the state of the forces exerted by the muscles in real time, and thus cannot be directly used for assistance in improving the swing motion.

SUMMARY OF THE INVENTION

Accordingly, the present invention is directed to a muscular energy state analysis system and method for a swing motion and a computer program product thereof, which are suitable for analyzing muscular performance of the swing motion of a user, and further providing a force-exertion suggestion, so as to enable the user to correct his/her swing posture and motion.

The present invention provides a muscular energy state analysis system for a swing motion, which includes: a swing implement, for a user to perform the swing motion, and including an acceleration sensor for sensing acceleration of the swing implement when the swing implement is swung, so as to generate a swing speed data; a plurality of signal detection modules, for detecting a plurality of electromyographic (EMG) signals generated by a plurality of muscles of the user; a database, for storing at least one muscular energy sample value, in which each muscular energy sample value at least includes a swing speed sample value and a plurality of corresponding muscular performance sample values; a muscular energy analysis module, for analyzing the EMG signals and the swing speed data to obtain a plurality of muscular performance values; and a comparison module, for comparing the swing speed data and the muscular performance values with the at least one muscular energy sample value in the database, so as to generate a comparison result data.

The present invention provides a muscular energy state analysis method for a swing motion, which includes: providing a database storing at least one muscular energy sample value, in which each muscular energy sample value at least includes a swing speed sample value and a plurality of corresponding muscular performance sample values; sensing acceleration of a swing implement by an acceleration sensor when a user uses the swing implement to perform the swing motion, so as to generate a swing speed data; obtaining a plurality of electromyographic (EMG) signals generated by a plurality of muscles of the user; analyzing the EMG signals and the swing speed data so as to obtain a plurality of muscular performance values; and comparing the swing speed data and the muscular performance values with the at least one muscular energy sample value in the database, so as to generate a comparison result data.

The present invention is characterized in that, the present invention is suitable for use in the field of sports involving swing motions to analyze a muscular state and muscular performance of the user in real time, so as to provide a comparison result data. Further, an appropriate suggestion is provided for the user by analyzing the comparison result data, so as to improve the overall swing efficiency. In addition, in the present invention, the EMG signals generated by the muscles when the user swings, so as to analyze the muscular state and muscular performance of the user, and then the data comparison module compares the muscular state and muscular performance with at least one muscular energy sample value to analyze the force of which muscle needs to be corrected, so as to provide the most appropriate force-exertion suggestion, thereby avoiding sports injuries and improving the training efficiency.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Preferred embodiments of the present invention are described in detail below with reference to the accompanying drawings.

Figure 1A:
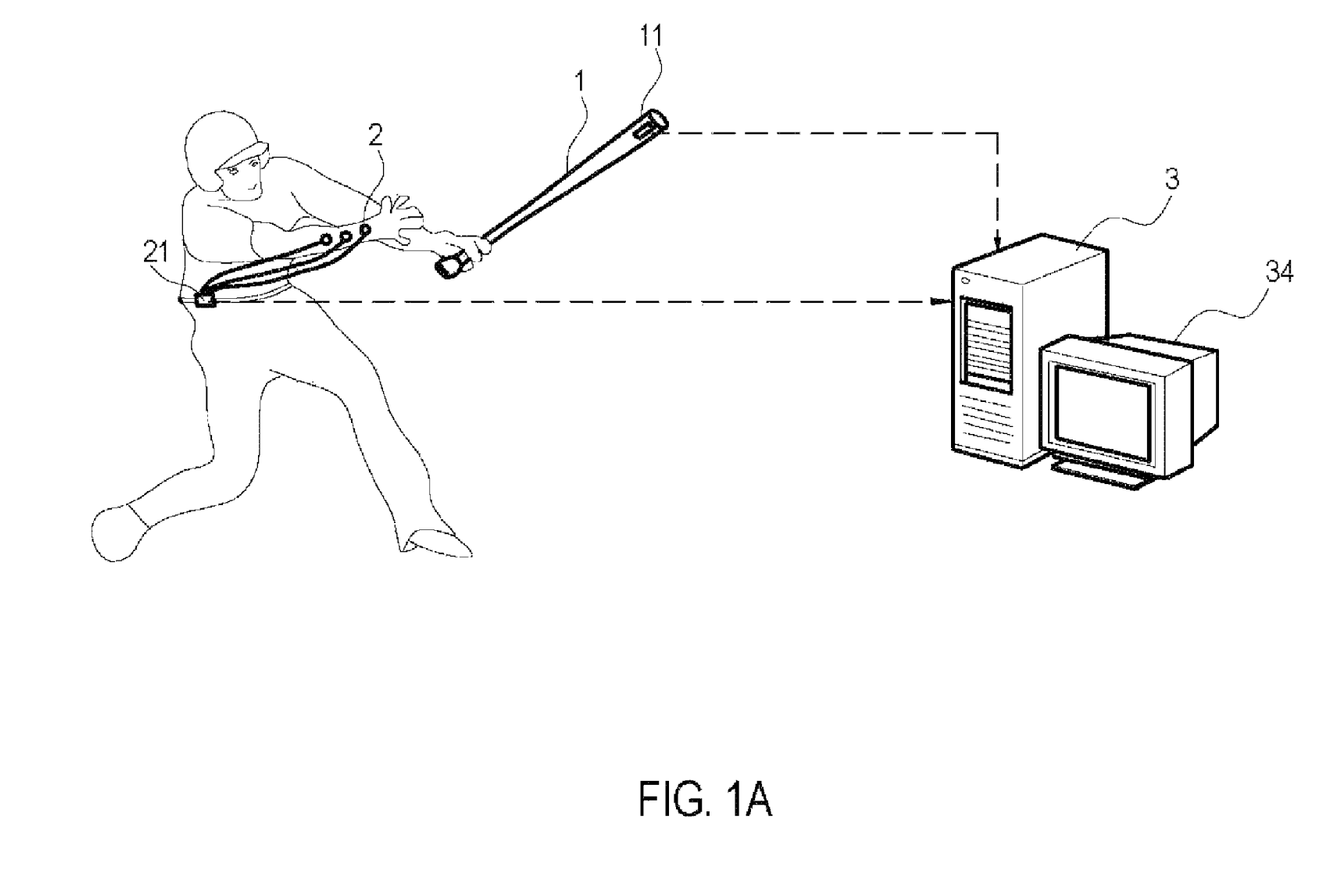
FIG. 1A is a graphical architectural view of a muscular energy state analysis system for a swing motion according to an embodiment of the present invention.
Figure 1B:
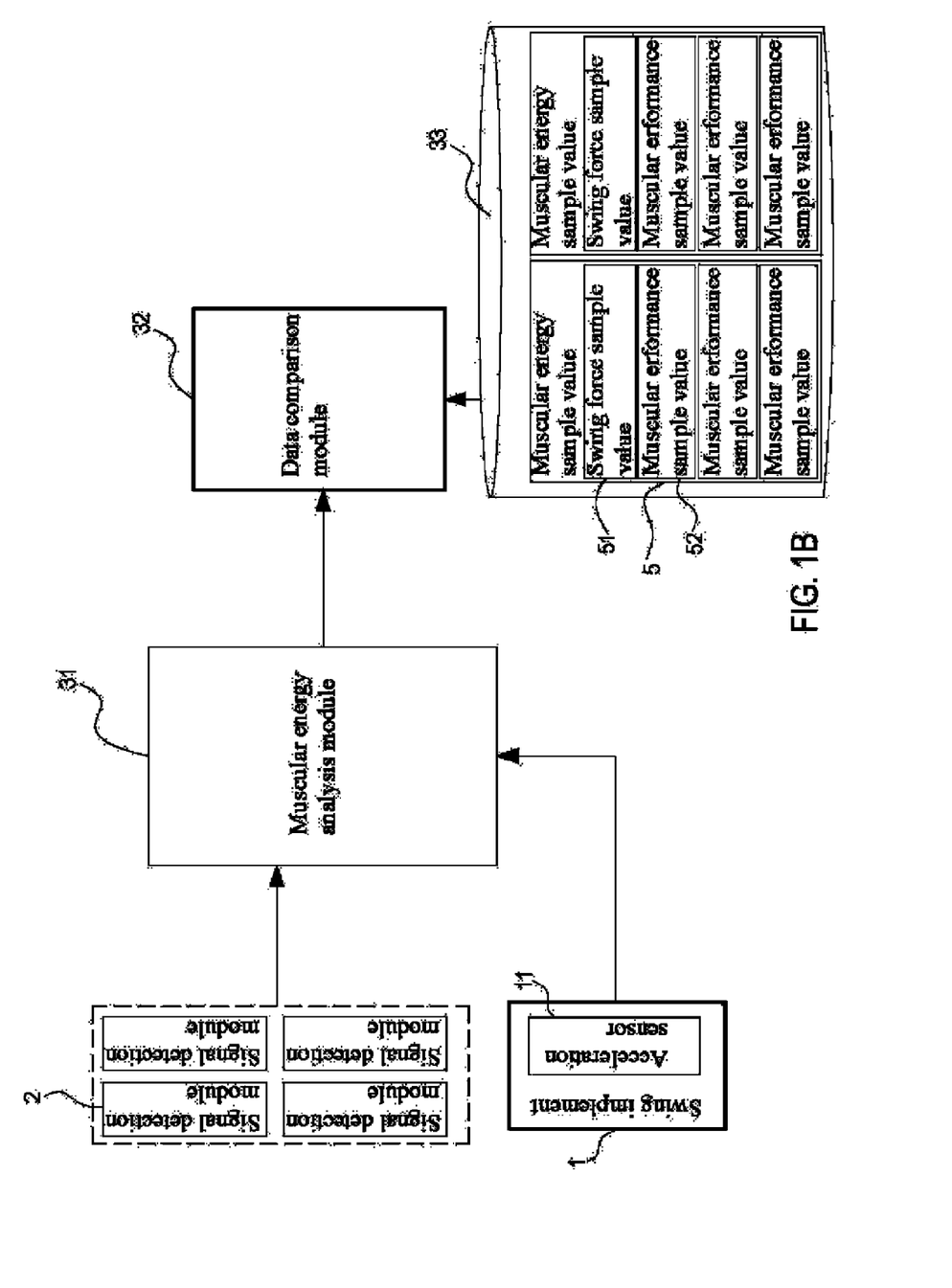
FIG. 1B is a block diagram of a muscular energy state analysis system for a swing motion according to an embodiment of the present invention.
Figure 1C:
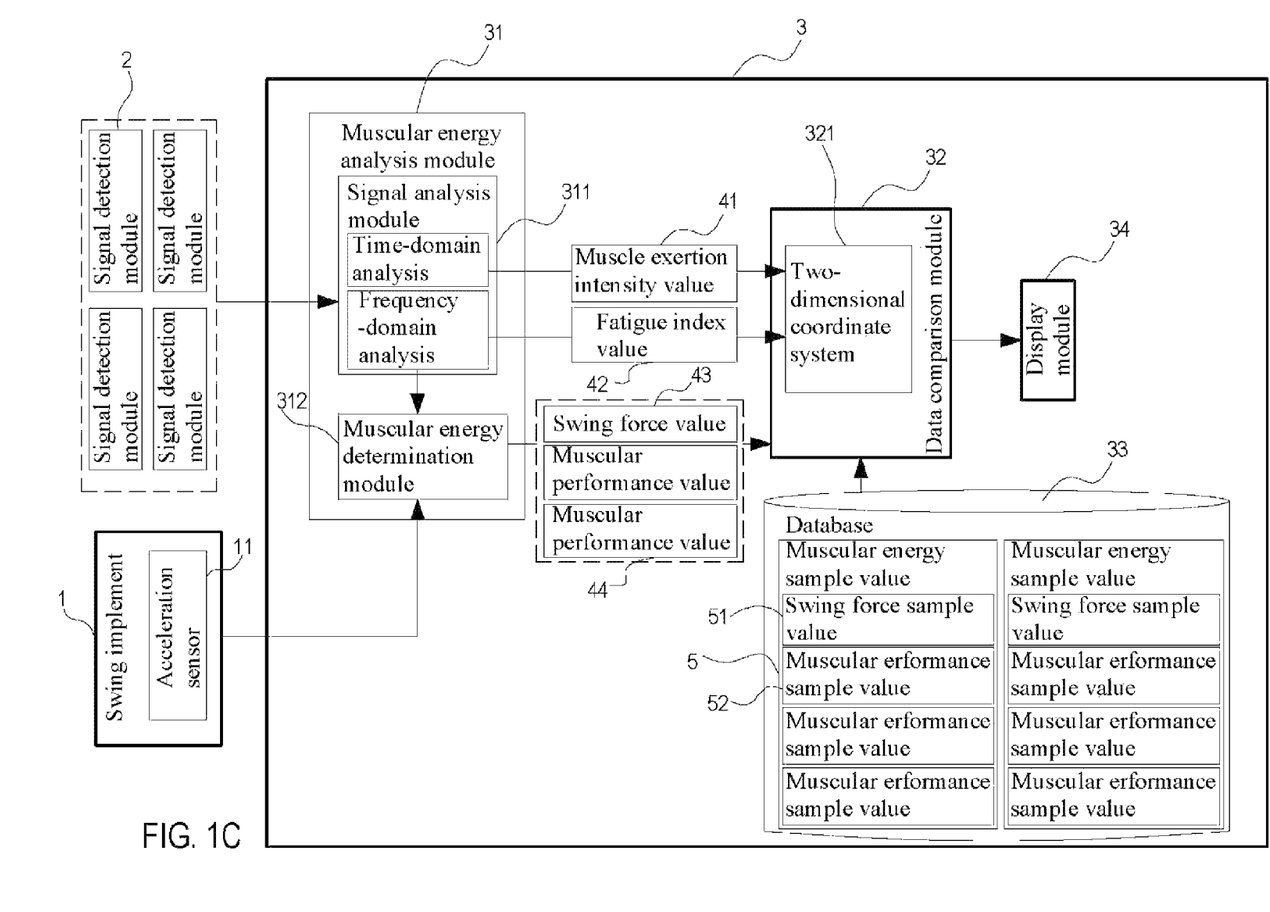
FIG. 1C is a block diagram of a muscular energy state analysis system for a swing motion according to another embodiment of the present invention.

FIG. 1A is a graphical architectural view of a muscular energy state analysis system for a swing motion according to an embodiment of the present invention, and FIG. 1B is a block diagram of a muscular energy state analysis system for a swing motion according to an embodiment of the present invention. FIG. 1C is a block diagram of a muscular energy state analysis system for a swing motion according to another embodiment of the present invention. Referring to FIGS. 1A, 1B and 1C, the system includes a swing implement 1, a plurality of signal detection modules 2, a database 33, a muscular energy analysis module 31 and a comparison module 32.

The swing implement 1 is used for a user to perform the swing motion. The swing implement 1 includes an acceleration sensor 11, which is a multi-dimensional accelerometer, for example, a two-dimensional accelerometer or a three-dimensional accelerometer. The swing implement 1 of this embodiment is described by taking a bat as an example; however, the present invention is not limited thereto, and the swing implement 1 may also be any device that can be used to perform a swing motion, such as a golf club, a tennis racket, and a badminton racket.

In this embodiment, the acceleration sensor 11 is disposed at an end of the bat, and is used for sensing a speed of the bat when a user swings the bat, so as to generate a swing speed data.

The signal detection modules 2 are described by taking sensor pads as an example, which are adhered to the body of the user for sensing EMG signals generated by relevant muscles when the user performs the swing motion. The muscles include more than one relevant muscle of shoulder, arm, breast, waist, wrist, thigh, leg, sole, and the like. In other embodiments, the signal detection modules 2 may be any commercially available EMG devices, equipment, systems or any related signal sensing elements, for example: wireless EMG equipments for acquainting, measuring and analyzing the surface EMG signals, blue-tooth 8-frequency instrument, any related surface EMG electrodes, EMG sensing instrument and its related surface electrode films. Moreover, according to the muscular requirements of the swing motion, the signal detection modules 2 are disposed at relevant muscles on the right or left half of the body. The EMG signals and the swing speed data 43 are transmitted to the muscular energy analysis module 31. The acceleration sensor 11, the signal detection modules 2 and the muscular energy analysis module 31 may connect using as the following modes:

1) The acceleration sensor 11, the signal detection modules 2 and the muscular energy analysis module 31 respectively includes a wireless communication module for wireless connection. Therefore, the swing speed data and the each EMG signal can be transmitted to the muscular energy analysis module 31 form the acceleration sensor 11, the signal detection modules 2; and 2) The database 33, the muscular energy analysis module 31 and the comparison module 32 was disposed in a computer 3. The computer 3 connects to the acceleration sensor 11 and each signal detection module 2 through a wire/wireless connection. For example, the computer 3 connects to each of the signal detection modules 2 through USB communication module, so as to obtain the swing speed data and the EMG signals. As shown in FIG. 1A and FIG. 1C, the acceleration sensor 11 and the signal detection modules 2 electrically coupled to a wireless transmitter 21, the wireless transmitter 21 connects wireless to the computer 3, in order to transmit the swing speed data and the EMG signals to the muscular energy analysis module 31. Here, the computer 3 can be a personal computer, a server, or a notebook computer. This embodiment is described by taking wireless connection as an example.

The database 33 stores at least one muscular energy sample value 5, each comprises the sample values of the forces and muscular energies generated by the muscles respectively when a standard swing motion is performed. Each muscular energy sample value 5 at least comprises a swing force sample value 51 and a plurality of corresponding muscular performance sample values 52.

In this embodiment, the muscular energy analysis module 31 mainly analyzes all the EMG signals and the swing speed data 43, so as to obtain a swing force value 43 and a plurality of muscular performance values 44, and transmits the swing speed data 43 and the muscular performance values 44 to the comparison module 32. The muscular energy analysis module 31 includes a signal analysis module 311 and a muscular energy determination module 312. The signal analysis module 311 is used for performing a time-domain analysis on the EMG signals so as to obtain a plurality of muscle exertion intensity values 41. A time-domain analysis formula is provided as follows, but the present invention is not limited thereto. The time-domain analysis formula is:

$$iEMG = \int_{T}^{T+t} EMG(t)dt \qquad \text{(Formula 1)}$$

In the formula, EMG is an electromyographic signal, iEMG is an integrated electromyographic activity of the muscles, and refers to a muscle exertion intensity value 41 here, and PSD is a frequency spectrum obtained from EMG through Fast Fourier Transform (FFT). The muscular performance value 44 is corresponding to each muscle group (muscle exertion intensity value 41/sum of muscle exertion intensity value 41)×100%.

Figure 2:
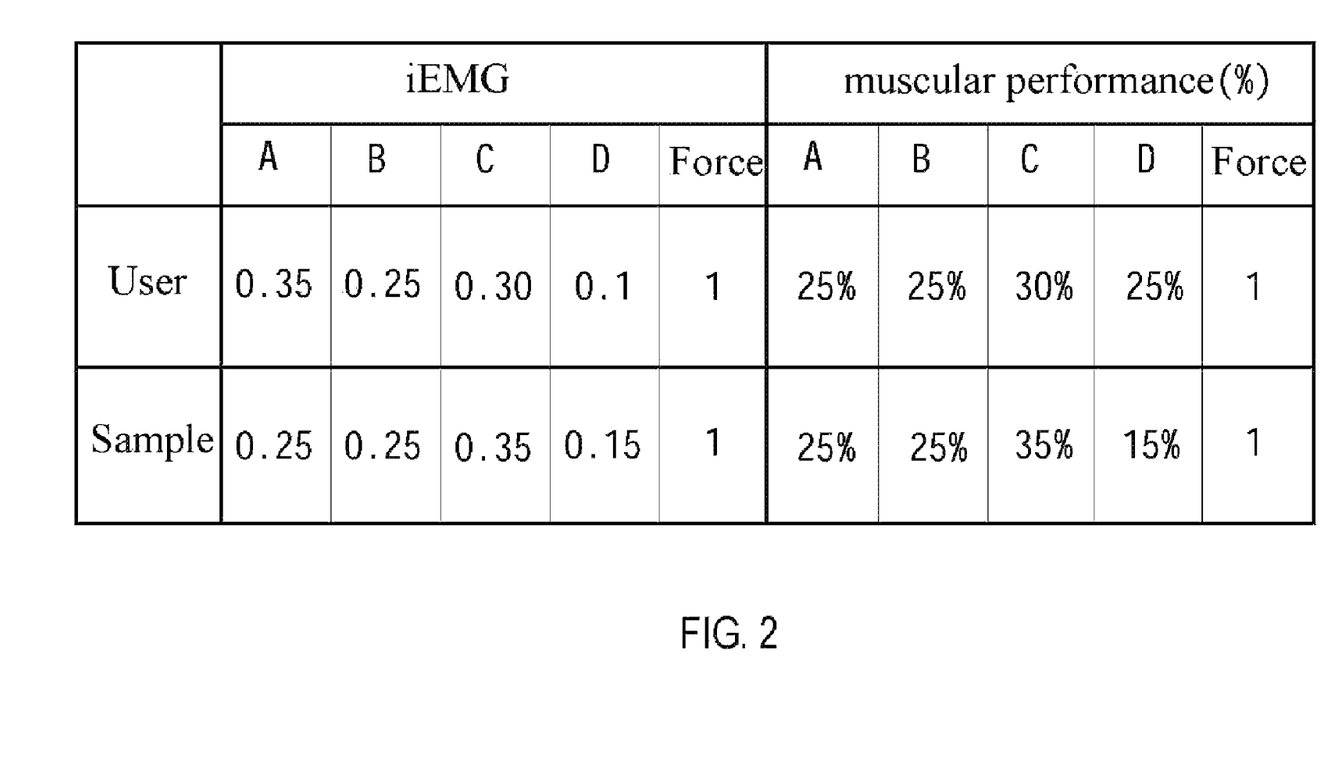
FIG. 2 is a graphical view of muscular performance comparison according to an embodiment of the present invention.

FIG. 2 is a graphical view of muscular performance comparison according to an embodiment of the present invention. Referring to FIG. 2, it is assumed that the muscle groups exerting forces include Muscle Group A, Muscle Group B, Muscle Group C, and Muscle Group D, the muscle exertion intensity values 41 are respectively A=0.35, B=0.25, C=0.30, and D=0.10, and the sum of the muscle exertion intensity values 41 is 1, so that the muscular performance value 44 of Muscle Group A is (0.35/1)*100%=35%, the muscular performance value 44 of Muscle Group B is (0.25/1)*100%=25%, the muscular performance value 44 of Muscle Group C is (0.30/1)*100%=30%, and the muscular performance value 44 of Muscle Group D is (0.1/1)*100%=10%.

After obtaining the swing force value 43 and the corresponding muscular performance values 44, the comparison module 32 reads the muscular energy sample values 5 in the database 33, compares the swing force value 43 with each of the swing force sample value 51 in the database 33, so as to find out a target muscular energy sample value 5 with a target force sample value 51 which is approximate or equal to the swing force sample value 43. The muscular performance values 44 and the corresponding muscular performance sample values 52 correspond to one of the plurality of muscular properties. The comparison module 32 compares the muscular performance values 44 with target performance sample values included in the target muscular energy sample values 5. For example, the muscular performance value 44 and the target performance sample value of the same muscular property of Muscle Group A are compared, the muscular performance value 44 and the target performance sample value of the same muscular property of Muscle Group B are compared, and so on. The compared result will be displayed on a display module 34. The result will be displayed by a value, a chart or a diagram, so as to display the difference between the swing speed data and the swing speed sample data, and the differences between muscular energy values and the muscular energy sample values.

The comparison module 32 determines whether the muscular performance values 44 include at least one abnormal muscular performance value 44 and obtains a comparison result data based on the difference between the swing speed data and the swing speed sample data, and the difference between muscular energy value and the muscular energy sample value. If yes, the comparison module 32 generates a force-exertion suggestion data according to the comparison result data. In this embodiment, if the determination is that abnormal muscular performance value 44 exists, the comparison module 32 generates a force-exertion suggestion data to suggest the user to adjust the muscle force-exertion mode; otherwise, the comparison module 32 does not perform any operation, or suggests the user to maintain the current force-exertion mode.

For example, when the target performance sample value of the muscular property of Muscle Group A is 25%, and the muscular performance value 44 of the muscular property of Muscle Group A (with the same muscular property) is 35%, the muscular performance value 44 is 10% greater than the target performance sample value. At this time, the comparison module 32 determines that the force exerted by Muscle Group A of the user is too large, and should be decreased. If the forces exerted by Muscle Group C and Muscle Group D are too small, which are also abnormal muscular performance values 44, and should be slightly increased. Accordingly, the comparison module 32 generates a force-exertion suggestion data to suggest the user to decrease the force exerted by Muscle Group A and slightly increase the forces exerted by Muscle Group C and Muscle Group D. The force-exertion suggestion data can be displayed on a display module 34 for reference by the user.

Moreover, the signal analysis module 311 further performs a frequency-domain analysis on the EMG signals so as to obtain a fatigue index value 42. During the frequency-domain analysis, firstly, the EMG signals are transformed into a frequency spectrum through FFT, which is then introduced into the following frequency-domain analysis formula (not limited thereto) so as to obtain the fatigue index value 42:

$$\int_0^{MDF} PSD(f)df = \int_{MDF}^{\infty} PSD(f)df = \frac{1}{2}\int_0^{\infty} PSD(f)df \quad \text{(Formula 2)}$$

In the formula, MDF refers to median frequency, and refers to a fatigue index value 42 here. MDF: when it is calculated in the frequency domain that the integrated area is equal to half of the total area, the point indicates that a frequency change of the muscles occurs at this time. That is, the original signals are transformed into a frequency spectrum through FFT, which may be used as a fatigue index representing muscle fatigue. When the muscles are in a fatigue state, the median frequency of the EMG signals will move towards lower frequencies.

Then, the comparison module 32 further forms a two-dimensional coordinate system 321 by using the muscle exertion intensity value 41 and the fatigue index value 42, and divides the two-dimensional coordinate system 321 into a plurality of quadrants. The comparison module 32 determines whether the user is in the fatigue state by analyzing a point P1 defined by the muscle exertion intensity value 41 and the fatigue index value 42 (x=muscle exertion intensity value 41, y=fatigue index value 42) and a quadrant where the point P1 is, and generates a rest suggestion information when the user is in the fatigue state.

Figure 3:
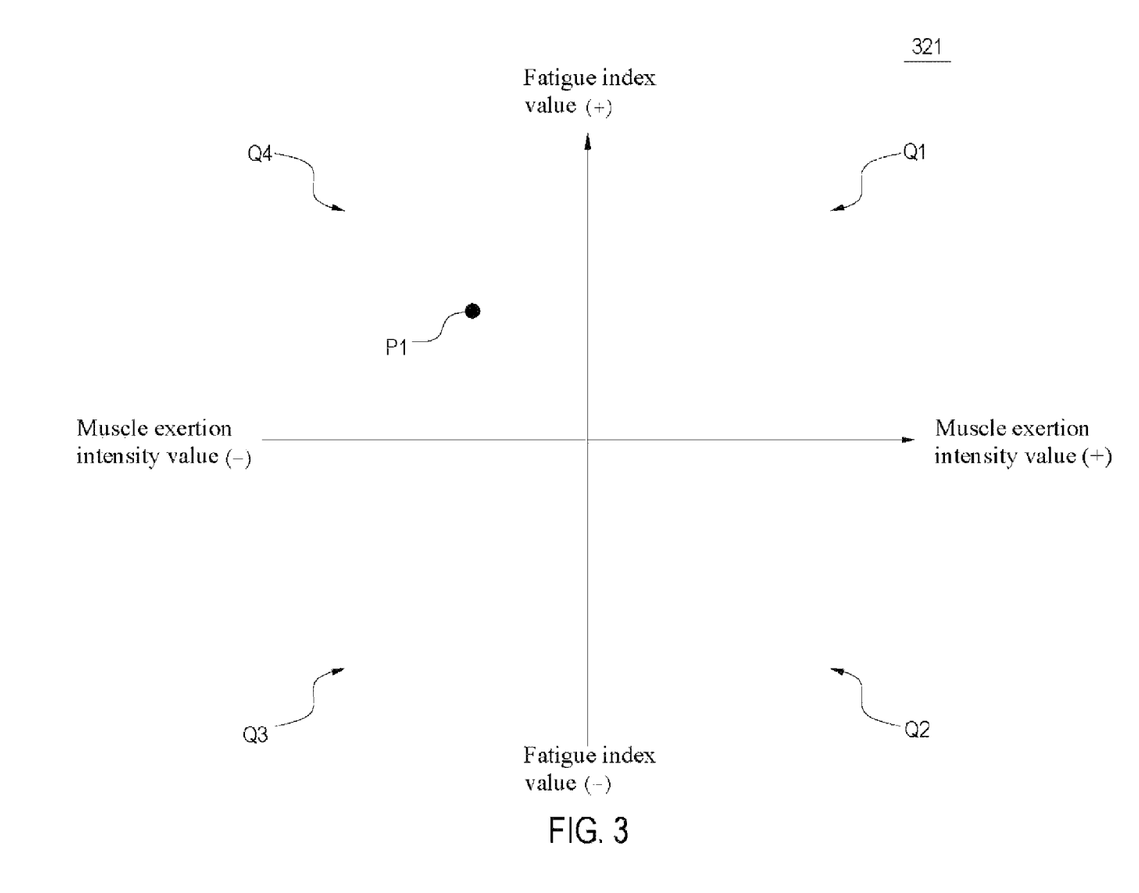
FIG. 3 is a graphical view of quadrants and a point of a two-dimensional coordinate system according to an embodiment of the present invention.

FIG. 3 is a graphical view of the quadrants and the point P1 of the two-dimensional coordinate system 321 according to an embodiment of the present invention. Referring to FIG. 3, the point P1 represents variation of the muscle exertion intensity value 41 and the fatigue index value 42 with time, that is, a slope, when the EMG signals measured at continuous times are taken in the time-domain analysis and frequency-domain analysis. The quadrants have the following meanings.

First quadrant Q1 (Force increase): If the slopes of the iEMG value and the MDF value with time are both positive, it indicates that the force exerted by the muscles increases as time goes on.

Second quadrant Q2 (Adaptation): If the slope of the iEMG value is negative and the slope of the MDF value is positive, it indicates that the muscles gradually adapt to the force exertion of the current swing motion as time goes on.

Third quadrant Q3 (Force decrease): If the slopes of the iEMG value and the MDF value with time are both negative, it indicates that the force exerted by the muscles decreases as time goes on.

Fourth quadrant Q4 (Fatigue): If the slope of the iEMG value is positive and the slope of the MDF value is negative, it indicates that the muscles are in the fatigue state as time goes on.

The comparison module 32 determines whether the user is in the fatigue state according to the quadrant where the point P1 is. When the point P1 is in the fourth quadrant Q4, the comparison module 32 determines that the user is in the fatigue state, and generates a rest suggestion information, which is displayed on the display module 34 for reference by the user.

Figure 4:
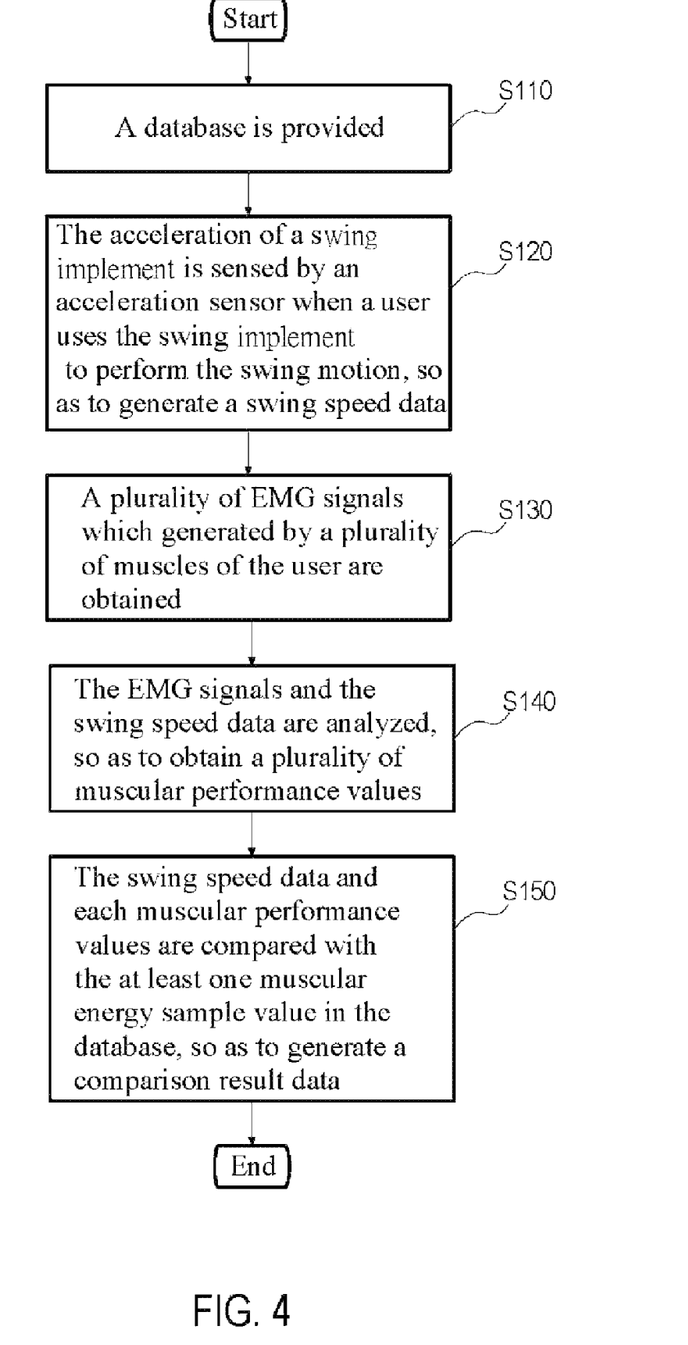
FIG. 4 is a flow chart of a muscular energy state analysis method for a swing motion according to an embodiment of the present invention.

FIG. 4 is a flow chart of a muscular energy state analysis method for a swing motion according to an embodiment of the present invention. Referring to FIGS. 1A-3 and 4, the muscular energy state analysis method for a swing motion according to this embodiment includes the following steps.

A database 33 is provided (Step S110). The database 33 stores at least one muscular energy sample values 5, which are values of the forces and muscular energies generated by the muscles when a standard swing motion is performed. Each muscular energy sample value 5 includes a swing force sample value 51 and a plurality of corresponding muscular performance sample values 52.

The acceleration of a swing implement 1 is sensed by an acceleration sensor 11 when a user uses the swing implement 1 to perform the swing motion, so as to generate a swing speed data. (Step S120). In this embodiment, the swing implement 1 is described by taking a bat as an example; however, the present invention is not limited thereto, and the swing implement 1 may also be any device that can be used to perform a swing motion, such as a golf club, a tennis racket, and a badminton racket. The acceleration sensor 11 is a multi-dimensional accelerometer, for example, a two-dimensional accelerometer or a three-dimensional accelerometer. The acceleration sensor 11 is disposed at an end of the bat, and is used for sensing a speed of the bat when a user swings the bat, so as to generate a swing speed data.

A plurality of electromyographic (EMG) signals which generated by a plurality of muscles of the user are obtained (Step S130). The signal detection modules 2 are described by taking sensor pads as an example, which are adhered to the body of the user for sensing EMG signals generated by muscles when the user performs the swing motion.

The EMG signals and the swing speed data 43 are analyzed, so as to obtain a plurality of muscular performance values 44 (Step S140). The EMG signals and the swing speed data 43 are transmitted to the muscular energy analysis module 31. For example, the acceleration sensor 11, the signal detection modules 2 and the muscular energy analysis module 31 may connect using as the following modes:

1) The acceleration sensor 11, the signal detection modules 2 and the muscular energy analysis module 31 respectively includes a wireless communication module for wireless connection. Therefore, the swing speed data and each EMG signal can be transmitted to the muscular energy analysis module 31 form the acceleration sensor 11, the signal detection modules 2; and 2) The database 33, the muscular energy analysis module 31 and the comparison module 32 was disposed in a computer 3. The computer 3 connects to the acceleration sensor 11 and each signal detection module 2 through a wire or wireless connection. For example, the computer 3 connects to each of the signal detection modules 2 through USB communication module, so as to obtain the swing speed data and the EMG signals. As shown in FIG. 1A and FIG. 1C, the acceleration sensor 11 and the signal detection modules 2 electrically coupled to a wireless transmitter 21, the wireless transmitter 21 connects wireless to the computer 3, in order to transmit the swing speed data and the EMG signals to the muscular energy analysis module 31. Here, the computer 3 can be a personal computer, a server, or a notebook computer. The embodiment will be illustrated using the second mode.

Figure 5:
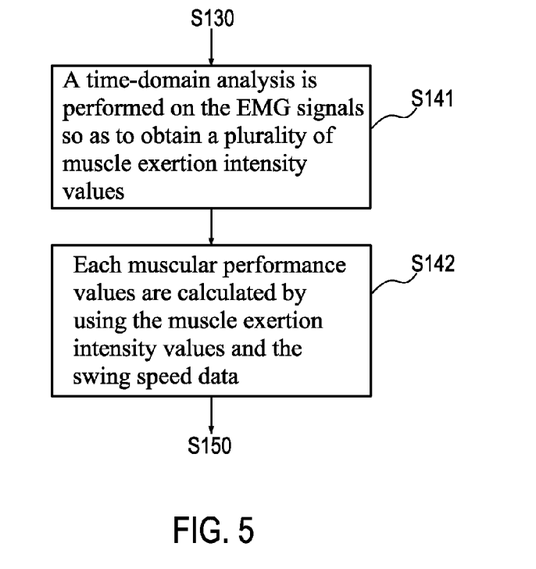
FIG. 5 is a detailed flow chart of Step S140 according to an embodiment of the present invention.

FIG. 5 is a detailed flow chart of Step S140 according to an embodiment of the present invention. Referring to FIG. 5, Step S140 includes the following substeps.

A time-domain analysis is performed on the EMG signals so as to obtain a plurality of muscle exertion intensity values 41 (Step S141). The muscular energy analysis module 31 includes a signal analysis module 311 and a muscular energy determination module 312. The signal analysis module 311 is used for performing a time-domain analysis on the EMG signals so as to obtain a plurality of muscle exertion intensity values 41. A time-domain analysis formula is provided as follows:

$$iEMG = \int_{T}^{T+t} EMG(t)dt \quad \text{(Formula 1)}$$

In the formula, EMG is an electromyographic signal, iEMG is an integrated electromyographic activity of the muscles, and refers to a muscle exertion intensity value 41 here, and PSD is a frequency spectrum obtained from EMG through FFT.

Each muscular performance values 44 are calculated by using the muscle exertion intensity values 41 and the swing speed data (Step S142). Each muscular performance value 44 corresponds to each muscle is (muscle exertion intensity value 41/sum of each muscle exertion intensity value 41)× 100%.

The swing speed data 43 and each muscular performance values 44 are compared with the at least one muscular energy sample value 5 in the database, so as to generate a comparison result data (Step S150). After obtaining the swing force value 43 and the corresponding muscular performance values 44, the comparison module 32 reads the muscular energy sample values 5 in the database 33, compares the swing force value 43 with each swing force sample value 51, so as to find out a target muscular energy sample value 5 including a target force sample value approximate or equal to the swing force sample value 51. The muscular performance values 44 and the corresponding muscular performance sample values 52 correspond to one of the plurality of muscular property. The comparison module 32 compares the muscular performance values 44 with target performance sample values included in the muscular energy sample values 5, that is, compares the muscular performance value 44 and the target performance sample value of the same muscular property one by one. For example, the muscular performance value 44 and the target performance sample value of the same muscular property of Muscle Group A are compared, the muscular performance value 44 and the target performance sample value of the same muscular property of Muscle Group B are compared, and so on. The compared result will be displayed on a display module 34. The result will be performed by a value, a chart or a diagram, so as to perform the difference between the swing speed data and the swing speed sample data, and the difference between muscular energy value and the muscular energy sample value.

Figure 6:
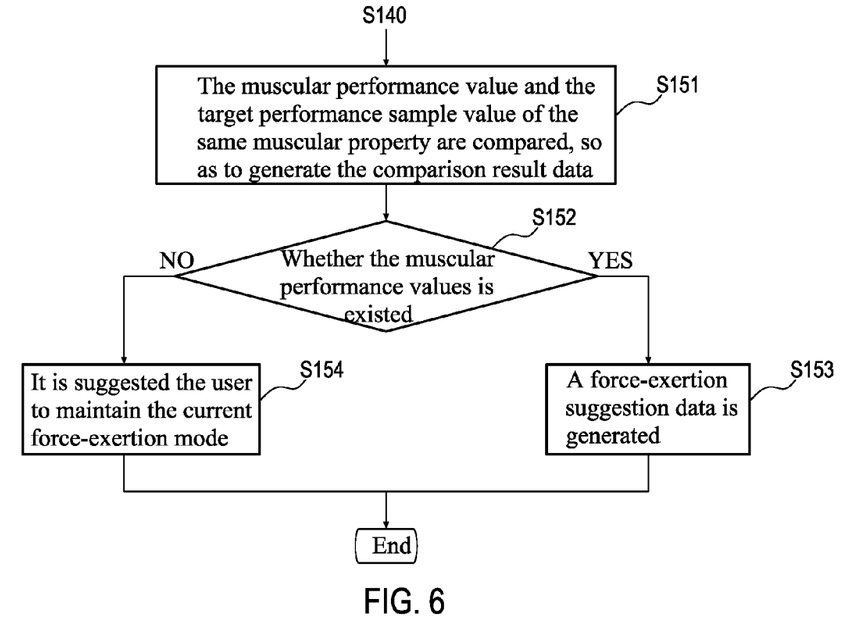
FIG. 6 is a detailed flow chart of Step S150 according to an embodiment of the present invention.

FIG. 6 is a detailed flow chart of Step S150 according to an embodiment of the present invention. In this embodiment, the muscular performance values 44 and the muscular performance sample values 52 are respectively corresponding to one of a plurality of muscular properties. Referring to FIG. 6, Step S150 includes the following substeps.

The muscular performance value 44 and the target performance sample value 52 of the same muscular property are compared, so as to generate the comparison result data (Step S151). The comparison module 32 compares the muscular performance values 44 and the target performance sample value 52 with each target muscular energy sample value 5, therefore, a target performance sample values is generated. After that, the muscular performance values 44 and the target performance sample value 52 are compared with the target performance sample value. The muscular performance value 44 and the target performance sample value 52 of the same muscular property are compared, so as to generate the comparison result data. The compared result will be displayed on a display module 34. The result will be performed by a value, a chart or a diagram, so as to perform the difference between the swing speed data 43 and the swing speed sample data 51, and the difference between muscular energy value 44 and the muscular performance sample values 52.

The comparison module 32 determines whether the muscular performance values 44 comprise at least one abnormal muscular performance by comparing the muscular performance values 44 with the muscular performance sample values (Step S152), and a force-exertion suggestion data is generated according to the comparison result data.

If the determination is that there is an abnormal muscular performance exit, the comparison module 32 generates a force-exertion suggestion data to suggest the user to adjust the muscle force-exertion mode (Step S153); otherwise, the comparison module 32 does not perform any operation, or suggests the user to maintain the current force-exertion mode (Step S154).

Figure 7:
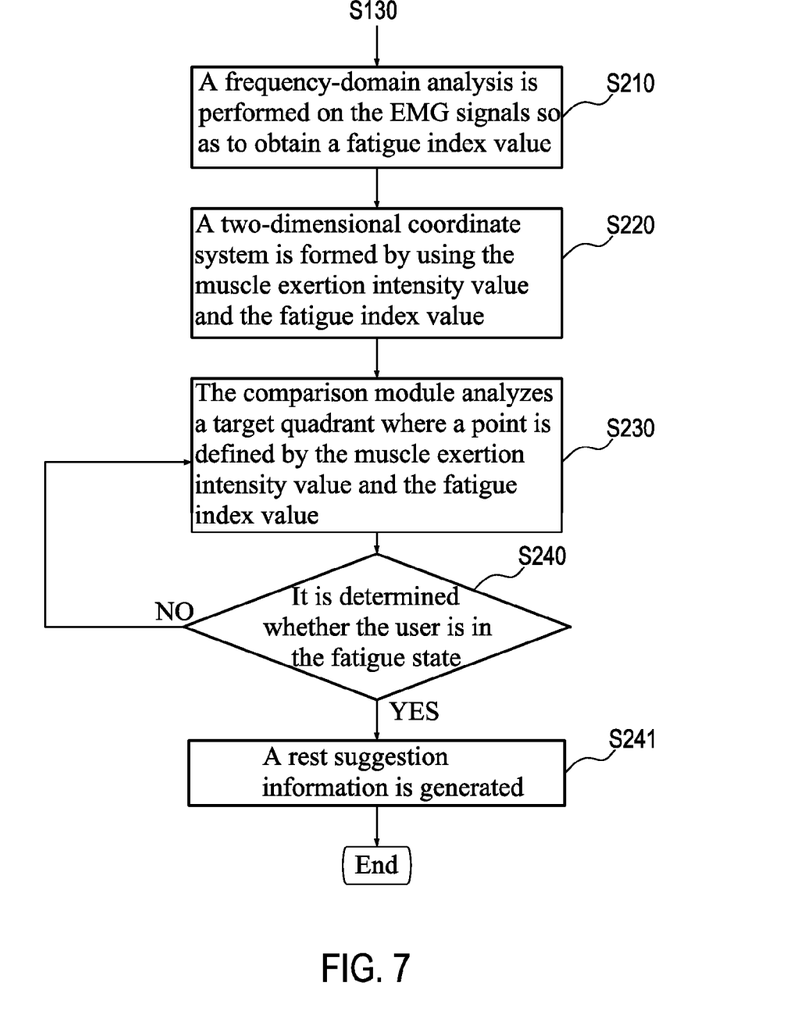
FIG. 7 is a flow chart of fatigue state analysis according to an embodiment of the present invention.

FIG. 7 is a flow chart of fatigue state analysis according to an embodiment of the present invention. Referring to FIGS. 1-4 and 7, the fatigue state analysis is performed after the EMG signals are obtained (that is, after Step S130), and includes the following steps.

A frequency-domain analysis is performed on the EMG signals so as to obtain a fatigue index value 42 (Step S210). The signal analysis module 311 further performs a frequency-domain analysis on the EMG signals so as to obtain a fatigue index value 42. During the frequency-domain analysis, firstly, the EMG signals are transformed into a frequency spectrum through FFT, and are introduced into the following frequency-domain analysis formula:

$$\int_0^{MDF} PSD(f)df = \int_{MDF}^{\infty} PSD(f)df = \frac{1}{2}\int_0^{\infty} PSD(f)df \quad \text{(Formula 2)}$$

In the formula, MDF refers to median frequency, and refers to a fatigue index value 42 here. MDF: when it is calculated in the frequency domain that the integrated area is equal to half of the total area, the point indicates that a frequency change of the muscles occurs at this time. That is, the original signals are transformed into a frequency spectrum through FFT, which may be used as a fatigue index representing muscle fatigue. When the muscles are in a fatigue state, the median frequency of the EMG signals will move towards lower frequencies.

A two-dimensional coordinate system 321 is formed by using the muscle exertion intensity value 41 and the fatigue index value 42 (Step S220). The two-dimensional coordinate system 321 is divided into a plurality of quadrants, with each quadrant representing different physiological states. The comparison module 32 analyzes a target quadrant where a point P1 defined by the muscle exertion intensity value 41 and the fatigue index value 42 is (Step S230). In this embodiment, the quadrants have the following meanings. First quadrant Q1 (Force increase): If the slopes of the iEMG value and the MDF value with time are both positive, it indicates that the force exerted by the muscles increases as time goes on. Second quadrant Q2 (Adaptation): If the slope of the iEMG value is negative and the slope of the MDF value is positive, it indicates that the muscles gradually adapt to the force exertion of the current swing motion as time goes on. Third quadrant Q3 (Force decrease): If the slopes of the iEMG value and the MDF value with time are both negative, it indicates that the force exerted by the muscles decreases as time goes on. Fourth quadrant Q4 (Fatigue): If the slope of the iEMG value is positive and the slope of the MDF value is negative, it indicates that the muscles are in the fatigue state as time goes on. The comparison module 32 determines whether the user is in the fatigue state according to the quadrant where the point P1 is (Step S240). In this embodiment, when the point P1 is in the fourth quadrant Q4, the comparison module 32 determines that the user is in the fatigue state. The comparison module 32 can even determine that the user is in the fatigue state when the point P1 is in the third quadrant Q3. When the comparison module 32 determines that the user is in the fatigue state, the comparison module 32 generates a rest suggestion information (Step S241) for reference by the user; otherwise, the process returns to Step S230, and the comparison module 32 detects the quadrant where the point P1 is again.

In conclusion, the above are only preferred implementations or embodiments of the present invention for presenting the technical solutions to solve the problems, but are not intended to limit the scope of the present invention. In view of the foregoing, it is intended that the present invention cover modifications and variations of this invention provided they fall within the scope of the following claims and their equivalents.

What is claimed is:

1. A muscular energy state analysis system for a swing motion, comprising:
    a swing implement, for a user to perform the swing motion, and comprising an acceleration sensor for sensing acceleration of the swing implement when the swing implement is swung, so as to generate a swing speed data;
    a plurality of signal detection modules, for detecting a plurality of electromyographic (EMG) signals generated by a plurality of muscles of the user;
    a database, for storing a muscular energy sample value, wherein the muscular energy sample value comprises a swing speed sample value and a plurality of corresponding muscular performance sample values;
    a muscular energy analysis module, for analyzing the EMG signals and the swing speed data so as to obtain a plurality of muscular performance values, wherein the muscular energy analysis module comprises a signal analysis module and a muscular energy determination module, the signal analysis module performs a time-domain analysis on the EMG signals so as to obtain a plurality of muscle exertion intensity values, and the muscular energy determination module calculates the muscular performance values by using the muscle exertion intensity values, wherein the signal analysis module further performs a frequency-domain analysis on the EMG signals so as to obtain a fatigue index value and forms a two-dimensional coordinate system by using one of the muscle exertion intensity values and the fatigue index value; and
    a comparison module, for comparing the swing speed data and the plurality of muscular performance values with the muscular energy sample value in the database, so as to generate a comparison result data, wherein the comparison module analyzes a target quadrant where a point defined by the muscle exertion intensity value and the fatigue index value is, the comparison module determines whether the user is in the a fatigue state according to the quadrant where the point is, and when the comparison module determines that the user is in the fatigue state, the comparison module generates a rest suggestion information.

2. The muscular energy state analysis system for a swing motion according to claim 1, wherein the comparison module compares the swing speed data and the plurality of muscular performance values with the swing speed sample value and the plurality of corresponding muscular performance sample values of each of the muscular energy sample values in the database respectively, so as to generate the comparison result data.

3. The muscular energy state analysis system for a swing motion according to claim 1, wherein the muscular performance values and the muscular performance sample values are respectively corresponding to one of a plurality of muscular properties; and the muscular energy analysis module compares the muscular performance value and the muscular performance sample value of the same muscular property, so as to generate the comparison result data.

4. The muscular energy state analysis system for a swing motion according to claim 1, wherein the muscular energy analysis module further determines whether the muscular performance values comprise an abnormal muscular performance value by comparing the muscular performance values with the muscular performance sample values.

5. The muscular energy state analysis system for a swing motion according to claim 4, wherein the comparison module further generates a force-exertion suggestion data according to the comparison result data.

6. The muscular energy state analysis system for a swing motion according to claim 1, wherein when comparing the swing speed data and the plurality of muscular performance values with the muscular energy sample value in the database, the comparison module compares the swing speed data and the plurality of muscular performance values with each of the muscular energy sample values in the database, selects a target muscular energy sample value from the muscular energy sample value, and compares the swing speed data and the plurality of muscular performance values with the target muscular energy sample value, so as to generate the comparison result data.

7. The muscular energy state analysis system for a swing motion according to claim 1, further comprising a display for displaying the comparison result data.

8. The muscular energy state analysis system for a swing motion according to claim 1, wherein the comparison result data is a difference between the swing speed data and the swing speed sample value, and a difference between the plurality of muscular performance values and the plurality of muscular performance sample values.

9. A muscular energy state analysis method for a swing motion, comprising:
  providing a database storing a muscular energy sample value, wherein each of the muscular energy sample values comprises a swing speed sample value and a plurality of corresponding muscular performance sample values;
  sensing acceleration of a swing implement by an acceleration sensor when a user uses the swing implement to perform the swing motion, so as to generate a swing speed data;
  obtaining a plurality of electromyographic (EMG) signals generated by a plurality of muscles of the user;
  analyzing the EMG signals and the swing speed data so as to obtain a plurality of muscular performance values;
  comparing the swing speed data and the plurality of muscular performance values with the muscular energy sample value in the database, so as to generate a comparison result data;
  performing a frequency-domain analysis on the EMG signals so as to obtain a fatigue index value;
  forming a two-dimensional coordinate system by using a muscle exertion intensity value and the fatigue index value;
  analyzing a target quadrant where a point defined by the muscle exertion intensity value and the fatigue index value is located by a comparison module;
  determining whether the user is in a fatigue state according to the quadrant where the point is by the comparison module; and
  when the comparison module determines that the user is in the fatigue state, generating a rest suggestion information by the comparison module.

10. The method according to claim 9, wherein the comparing comprises:
  comparing the swing speed data and the muscular performance values with the swing speed sample value and the plurality of corresponding muscular performance sample values of the muscular energy sample value in the database, so as to generate the comparison result data.

11. The method according to claim 9, wherein the muscular performance values and the muscular performance sample values are respectively corresponding to one of a plurality of muscular properties, and the method further comprises:
  comparing the muscular performance value and the muscular performance sample value of the same muscular property, so as to generate the comparison result data.

12. The method according to claim 9, further comprising:
  determining whether the muscular performance values comprise an abnormal muscular performance value by comparing the muscular performance values with the muscular performance sample values.

13. The method according to claim 12, further comprising:
  generating a force-exertion suggestion data according to the comparison result data.

14. The method according to claim 9, wherein the comparing comprises: comparing the swing speed data and the plurality of muscular performance values with each of the muscular energy sample values in the database, selecting a target muscular energy sample value from the muscular energy sample value, and comparing the swing speed data and the plurality of muscular performance values with the target muscular energy sample value, so as to generate the comparison result data.

15. The method according to claim 9, further comprising:
  providing a display for displaying the comparison result data.

16. The method according to claim 9, wherein the comparison result data is a difference between the swing speed data and the swing speed sample value, and a difference between the plurality of muscular performance values and the plurality of muscular performance sample values.

17. A computer program product, for performing a muscular energy state analysis method for a swing motion when an electronic device reads the computer program product, wherein an acceleration sensor senses an acceleration of a swing implement when a user uses the swing implement to perform the swing motion, so as to generate a swing speed data, and a plurality of signal detection modules obtains a plurality of electromyographic (EMG) signals generated by a plurality of muscles of the user; and the method comprises:
  providing a database for storing a muscular energy sample value, wherein each of the muscular energy sample values comprises a swing speed sample value and a plurality of corresponding muscular performance sample values;
  analyzing the EMG signals and the swing speed data so as to obtain a plurality of muscular performance values;
  comparing the swing speed data and the plurality of muscular performance values with the muscular energy sample value in the database, so as to generate a comparison result data;

performing a frequency-domain analysis on the EMG signals so as to obtain a fatigue index value;

forming a two-dimensional coordinate system by using a muscle exertion intensity value and the fatigue index value;

analyzing a target quadrant where a point defined by the muscle exertion intensity value and the fatigue index value is located by a comparison module;

determining whether the user is in a fatigue state according to the quadrant where the point is by the comparison module; and when the comparison module determines that the user is in the fatigue state, generating a rest suggestion information by the comparison module.

* * * * *